(12) United States Patent
Giron et al.

(10) Patent No.: US 10,610,463 B2
(45) Date of Patent: Apr. 7, 2020

(54) PROCESS FOR PRODUCING A COSMETIC COMPOSITION

(71) Applicant: L'OREAL, Paris (FR)

(72) Inventors: Franck Giron, Lagny sur Marne (FR); Henri Samain, Bievres (FR); Franck Girier Dufournier, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/061,950

(22) PCT Filed: Dec. 8, 2016

(86) PCT No.: PCT/EP2016/080339
§ 371 (c)(1),
(2) Date: Jun. 13, 2018

(87) PCT Pub. No.: WO2017/102563
PCT Pub. Date: Jun. 22, 2017

(65) Prior Publication Data
US 2018/0369077 A1    Dec. 27, 2018

(30) Foreign Application Priority Data

Dec. 18, 2015   (FR) ..................... 15 62871

(51) Int. Cl.
| | | |
|---|---|---|
| A61Q 1/02 | (2006.01) | |
| A61Q 1/06 | (2006.01) | |
| B41M 5/00 | (2006.01) | |
| A61K 8/02 | (2006.01) | |
| B41M 5/025 | (2006.01) | |

(52) U.S. Cl.
CPC ............ *A61K 8/022* (2013.01); *A61K 8/0229* (2013.01); *A61Q 1/02* (2013.01); *A61Q 1/06* (2013.01); *B41M 5/0047* (2013.01); *B41M 5/0256* (2013.01); *A61K 2800/43* (2013.01); *A61K 2800/80* (2013.01)

(58) Field of Classification Search
None
See application file for complete search history.

(56) References Cited

U.S. PATENT DOCUMENTS

| | | | |
|---|---|---|---|
| 4,804,719 A | 2/1989 | Weaver et al. | |
| 4,999,418 A | 3/1991 | Krutak et al. | |
| 5,030,708 A | 7/1991 | Krutak et al. | |
| 5,032,670 A | 7/1991 | Parham et al. | |
| 5,043,376 A | 8/1991 | Sharma et al. | |
| 5,102,980 A | 4/1992 | Krutak et al. | |
| 5,104,913 A | 4/1992 | Sharma et al. | |
| 5,106,942 A | 4/1992 | Krutak et al. | |
| 5,194,463 A | 3/1993 | Krutak et al. | |
| 5,281,659 A | 1/1994 | Weaver et al. | |
| 6,585,365 B1* | 7/2003 | MacMillan | B41M 5/52 347/100 |
| 2005/0229811 A1* | 10/2005 | Kato | C09D 11/38 106/31.43 |
| 2011/0300196 A1 | 12/2011 | Fatemah | |
| 2014/0184686 A1* | 7/2014 | Writt | B41J 3/60 347/19 |
| 2015/0314141 A1 | 11/2015 | Grace | |
| 2015/0360016 A1* | 12/2015 | Rabe | A61B 5/0077 604/290 |

FOREIGN PATENT DOCUMENTS

| | | |
|---|---|---|
| EP | 0 669 323 A1 | 8/1995 |
| EP | 1 048 282 A1 | 11/2000 |
| FR | 2 528 420 A1 | 12/1983 |
| FR | 2 639 347 A1 | 5/1990 |
| FR | 2759941 A1 | 8/1998 |
| FR | 3015891 A1 | 7/2015 |
| WO | 92/07913 A1 | 5/1992 |
| WO | 2015/097620 A1 | 7/2015 |
| WO | 2015/168524 A1 | 11/2015 |

OTHER PUBLICATIONS

Sampling entry from Merriam Webster Dictionary 2011 (Year: 2011).*
International Search Report dated Jan. 31, 2017 in International Patent Application No. PCT/EP2016/080339 (4 pages).
Written Opinion dated Jan. 31, 2017 in International Patent Application No. PCT/EP2016/080339 (7 pages).
TechCrunch: "Print Your Own Makeup with Mink: Disrupt NY 2014," May 5, 2014, URL: https://www.youtube.com/watch?v=cBZHFUQiP8Q, retrieved on Jun. 28, 2016 (2 pages).

* cited by examiner

*Primary Examiner* — Robert A Wax
*Assistant Examiner* — Caralynne E Helm
(74) *Attorney, Agent, or Firm* — Shumaker, Loop & Kendrick, LLP

(57) ABSTRACT

A process for producing a cosmetic composition that includes step a) inkjet printing onto a basic cosmetic composition, using an inkjet printer, at least one fluid composition in an amount chosen so as to impregnate the basic composition over only a part of its thickness, and step b), after at least one sampling of the impregnated layer, repeating step a) while optionally modifying the fluid composition inkjet-printed.

19 Claims, 1 Drawing Sheet

PROCESS FOR PRODUCING A COSMETIC COMPOSITION

TECHNICAL FIELD

The present invention relates to the personalized colouration of a cosmetic composition by inkjet printing at least one ink onto the composition.

BACKGROUND

Most cosmetic products, and in particular makeup products, come in various shades. Even with a considerable choice of shades, it's sometimes difficult to find the shade suitable for a given situation. To solve this problem, a large number of shades can be purchased, but this is an expensive practice, the products take up space, and this also requires knowledge of how to find the suitable shade.

International application WO 2015/168524 describes a process consisting in taking a basic cosmetic composition, and, by means of an inkjet printer, covering it with a colouring composition. The printer can be equipped with colouring ink cartridges and also with cartridges containing a compound other than ink, for example a fragrance, a wax or an oil. The printing is carried out over the entire surface of the basic composition. The basic composition can be a free or compact powder, or a liquid, for example a cream.

SUMMARY

There is a need for a process that is easy to carry out for a consumer and that makes it possible to adjust the colour or the composition at the rhythm desired by the consumer, in particular day-to-day.

Processes

A subject of the present invention is thus, according to one aspect, a process for producing a cosmetic composition, comprising the following steps:

a) inkjet printing onto a basic cosmetic composition, using an inkjet printer, at least one fluid composition in an amount chosen so as to impregnate the basic composition over only a part of its thickness, b) after at least one sampling of the impregnated layer, repeating step a) while optionally modifying the fluid composition inkjet-printed.

By virtue of the invention, it is possible to use a single basic cosmetic composition that can be printed a first time, to sample the impregnated layer, then to print again, so as for example to change fluid composition colour or formula, until the basic composition is exhausted. The invention applies to any makeup product for colouring the skin, the hair or the eyelashes.

Of course, step b) can be repeated several times, in particular until the basic composition is exhausted.

The basic composition is for example contained in a small dish during printing, the printer having a housing suitable for receiving said small dish.

The fluid composition printed can be stored in an electronic memory. In this case, step b) can comprise the depositing of the fluid composition stored.

The printing in step a) and/or b) can be carried out according to fluid compound information, in particular colour information, entered by the user, in particular selected on a screen, or measured, in particular on said user's skin.

The process can also comprise the step consisting in generating information relating to the wear of the impregnated layer. This information is, for example, generated automatically by image analysis on the basis of an observation of the coloured composition.

The process can comprise the step consisting in repairing and optionally storing the surface portion(s) of basic composition where the impregnated layer is at least partially exhausted. In this case, the printing in step b) can be carried out so as to impregnate only this or these surface portion(s).

The process can comprise the step consisting in helping a user in the selection of a fluid composition, in particular of an ink colour, to be inkjet-printed in step a) and/or b).

When the process is carried out by changing the printing colour, the choice of the new colour may depend on the colour previously printed. In particular, the process can comprise the step consisting in proposing a new colour to the user on the basis of the last colour produced by printing, and of the ink(s) available in the printer. Thus, the choice of a new colour by the user can only be made among the colours attainable by further printing on the remaining composition. The user can be invited to replace the support and to introduce a new basic composition if the desired colour is not attainable given the existing colour.

For example, if the basic composition is white and a first red printing is carried out at its surface, and if after application some thereof remains and the user wishes to modify the colour, then it may be automatically proposed to said user to go towards a shade that is more in the violet or orange range if blue and yellow inks are available in the printer. On the other hand, if the user wishes a green colour, then the latter may be invited to start from a new white basic composition.

Another subject of the invention, according to another of its aspects, in combination with the aforementioned, is a process for making up human keratin materials, in which a cosmetic composition is produced by carrying out step a) of the process as defined above, this composition is applied to the keratin materials and step b) is carried out.

In this process, step a) can be repeated while modifying the colour of the fluid composition printed, the choice of the new colour printed being made according to the result of the application with the preceding colour.

As a variant, step a) can be repeated while retaining the colour of the fluid composition printed, the amount inkjet-printed being greater.

Basic Cosmetic Composition

The basic composition may be pulverulent or non-pulverulent.

The basic composition may be white or non-white.

The basic composition may be in the form of a compact powder, a stick, a pencil or felt pen or in the form of a cream.

The basic composition may comprise any customary compound used in cosmetic compositions.

For obvious reasons, the choice of the nature and amount of these compositions is clearly within the competence of those skilled in the art.

For example, the composition may comprise mineral powders, and in particular talc, perlite, mica, clays, kaolin, aerogels, silica beads, zeolites and mixtures thereof.

The composition may also comprise powdered organic compounds, for example starch, flours, nylon and mixtures thereof.

The composition may also comprise glycols or esters, such as caprylyl glycol, oils, for example dimethicones, organic polymers, solvents and mixtures thereof.

The term "compact powder" is intended to mean a mass of product of which the cohesion is at least partly provided by compacting or pressing during the manufacture. In particular, by taking a measurement using a TA.XTplus Texture Analyser texturometer sold by the company Stable Micro Systems, the compact powder according to the invention may advantageously have a pressure resistance of between 0.1 and 2.5 kg and in particular between 0.2 and 1.0 kg, relative to the surface area of the spindle used (in the present case 7.07 mm$^2$). The measurement of this resistance is performed by moving an SMS P/3 flat-headed cylindrical spindle over a distance of 1.5 mm and at a speed of 0.5 mm/second in contact with the powder.

The basic composition may be a foundation, a blusher or a lipstick. The composition according to the invention is a makeup product, preferably of foundation, makeup base, face powder, eyeshadow, concealer product or blusher.

Fluid Composition

The amount of fluid composition inkjet-printed in step a) can be greater than or equal to 5 mg/cm$^2$.

For the purposes of the invention, the description "fluid" is intended to characterize the fact that a composition according to the invention is not solid. In other words, it manifests a fluidity sufficient to have flow properties. In particular, the composition according to the invention may advantageously have a viscosity of less than 100 Pa·s, preferably between 0.1 Pa·s and 50 Pa·s, and better still between 1 Pa·s and 30 Pa·s, at ambient temperature and pressure, the viscosity being in particular measured using a Rheomat RM100® instrument.

Ink

In one particular embodiment, the fluid composition is a cosmetic ink. In this case, the basic cosmetic composition is given colour.

The colour of the fluid composition printed in step a) can be different from the colour printed in step b). This change of colour or shade can make it possible to adapt to a tanning colour for example of the consumer's skin, or to another colour desire.

The ink(s) inkjet-printed on the basic cosmetic composition, in step a), is (are) advantageously one or more aqueous inks, comprising a weight concentration of at least 50% of water. The ink(s) can comprise an additional hydrophilic solvent chosen from alcohols, such as lower monoalcohols having from 1 to 5 carbon atoms such as ethanol and isopropanol, glycols having from 2 to 8 carbon atoms, such as ethylene glycol, propylene glycol, 1,3-butylene glycol and dipropylene glycol, $C_3$ and $C_4$ ketones, in particular acetone, and $C_2$-$C_4$ aldehydes and polyols, for example chosen from ethylene glycol, pentaerythritol, trimethylolpropane, propylene glycol, 1,3-propanediol, butylene glycol, isoprene glycol, pentylene glycol, hexylene glycol, glycerol, polyglycerols, such as glycerol oligomers, for instance diglycerol, polyethylene glycols, and mixtures thereof.

The ink(s) inkjet-printed onto the basic cosmetic composition is (are) advantageously offset inks, inks for flexography and photogravure, containing alcohols such as propanol, ethanol or butanol, glycol esters, alkyl acetates, ketones such as acetone or diacetone alcohol, and mixtures thereof.

The or each ink comprises a colorant. The colorant may be present in the ink in a weight content ranging from 0.01% to 60%, preferably ranging from 0.1% to 40%, or even from 0.1% to 30% and preferentially ranging from 0.5% to 20%, relative to the total weight of the ink.

The ink may comprise one or more colorants chosen from water-soluble dyes and liposoluble dyes.

Among the water-soluble dyes, mention may be made of the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll and methylene blue.

Among the liposoluble dyes, mention may be made of Sudan Red III (CTFA: D&C Red 17), lutein, quinizarine green (CTFA: D&C Green 6), alizurol purple SS (CTFA: D&C Violet 2), Sudan Brown, D&C Yellow 11, D&C Orange 5, quinoline yellow, curcumin, and carotenoid derivatives such as lycopene, beta-carotene, bixin or capsanthin, and mixtures thereof. The colouring polymers are generally copolymers based on at least two different monomers, at least one of which is a monomeric organic dye. Such polymeric dyes are known to those skilled in the art. Reference may be made, for example, to the following documents: U.S. Pat. Nos. 5,032,670; 4,999,418; 5,106,942; 5,030,708; 5,102,980; 5,043,376; 5,104,913; 5,281,659, 5,194,463; 4,804,719; WO 92/07913, or else EP 1 048 282.

The ink according to the invention constitutes a cosmetically acceptable medium, i.e. a medium that is compatible with keratin materials such as the skin of the face or the body, the lips, the hair, the eyelashes, the eyebrows and the nails.

The ink may be liquid at the time of printing and may have, for example, a viscosity ranging from 1 mPa·s to 500 mPa·s and preferably from 1 mPa·s to 300 mPa·s at 25° C.

The viscosity of an ink of the invention may be measured according to any process known to those skilled in the art, and in particular according to the following conventional process. At 25° C. using a Rheomat 180 viscometer, equipped with a spindle rotating at 200 rpm, those skilled in the art choose the spindle for measuring the viscosity from the spindles M1, M2, M3 and M4 on the basis of his general knowledge, so as to be able to perform the measurement.

The ink may be in emulsion form.

The ink may be chosen from those that are sold for the Gatocopy food-grade printer, in particular of reference A426.

Other Fluid Compound

The fluid composition can comprise at least one compound chosen from the list made up of cosmetic and/or dermatological active agents.

As active agents that are suitable for use in the present invention, mention may be made in particular of:
  anti-aging/anti-wrinkle agents,
  moisturizers (or humectants),
  fragrances,
  neutralizers,
  emollients,
  binders, in particular water-soluble polymers or polymers in latex form,
  free-radical scavengers,
  coalescence agents,
  vitamins,
  screening agents, in particular sunscreens,
  anti-pollution agents and/or free-radical scavengers,
  agents acting on the microcirculation,
  agents acting on the energy metabolism of cells,
  hyaluronic acid,
  anti-glycation agents,
  NO-synthase inhibitors,
  agents for stimulating the synthesis of dermal or epidermal macromolecules and/or for preventing their degradation,
  agents for stimulating fibroblast and/or keratinocyte proliferation or for stimulating keratinocyte differentiation,
  muscle relaxants (dermo-relaxing agents and/or dermo-decontracting agents), tensioning agents,
desquamating agents,
depigmenting or propigmenting agents,
anti-seborrhoea and anti-*P. acnes* active agents,
antioxidants and free-radical scavengers,
saccharides,
oligosaccharides, polysaccharides, which are hydrolysed or non-hydrolysed, and modified or unmodified,
amino acids, oligopeptides, peptides, proteins which are hydrolysed or non-hydrolysed, and modified or unmodified, polyamino acids, enzymes,
animal, plant or mineral waxes,
ceramides and pseudoceramides,
hydroxylated organic acids,
soluble or dispersed anionic polymers,
soluble or dispersed non-ionic polymers,
calmatives, and
mixtures thereof.

The fluid composition can in particular comprise at least one compound chosen from fragrances, UV-screening agents, moisturizers, binders, and mixtures thereof.

The amount of cosmetic and/or dermatological active agent(s) obviously depends on the nature of the active agent and on the desired effect, but said active agent(s) generally represent(s) from 0.1% to 40% by weight, relative to the total weight of the composition.

In the case with the compound as a fragrance, the fragrance may be water-soluble or hydrophobic and peptized.

By way of UV-screening agents, mention may in particular be made of those chosen from water-soluble UV-screening agents, liposoluble UV-screening agents, insoluble UV-screening agents, and mixtures thereof. Among these UV-screening agents, a distinction can be made between water-soluble organic screening agents, liposoluble organic screening agents, insoluble organic screening agents and inorganic screening agents.

Preferably, it is a water-soluble UV-screening agent or an inorganic UV-screening agent.

Among the water-soluble organic UVA-screening agents that can be used according to the present invention, mention may be made of benzene-1,4-di(3-methylidene-10-camphorsulfonic) acid (INCI name: Terephthalylidene Dicamphor Sulfonic Acid) and the various salts thereof, described in particular in patent applications FR 2 528 420 and FR 2 639 347, compounds comprising at least two benzoazolyl groups comprising sulfonic groups, such as those described in patent application EP 0 669 323, and benzophenone compounds comprising at least one sulfonic acid function.

The water-soluble organic UVB-screening agents are in particular chosen from water-soluble cinnamic derivatives, such as ferulic acid or 3-methoxy-4-hydroxycinnamc acid; water-soluble benzylidenecamphor compounds; water-soluble phenylbenzimidazole compounds; water-soluble p-aminobenzoic (PABA) compounds and water-soluble salicylic compounds.

The inorganic UV-screening agents used in accordance with the present invention are metal oxide pigments. They may be chosen in particular from titanium oxide, zinc oxide, iron oxide, zirconium oxide and cerium oxide, or mixtures thereof.

According to the invention, titanium dioxide pigments, in particular in dispersion, are particularly preferred.

The term "moisturizer" or "humectant" is intended to mean:
either a compound which acts on the barrier function, for the purpose of maintaining the hydration of the stratum corneum, or an occlusive compound. Mention may be made of ceramides, sphingoid-based compounds, lecithins, glycosphingolipids, phospholipids, cholesterol and derivatives thereof, phytosterols (stigmasterol, β-sitosterol, campesterol), essential fatty acids, 1,2-diacylglycerol, 4-chromanone, pentacyclic triterpenes such as ursolic acid, petroleum jelly and lanolin;

or a compound which directly increases the water content of the stratum corneum, such as threalose and derivatives thereof, hyaluronic acid and derivatives thereof, glycerol, pentanediol, sodium pidolate, serine, xylitol, sodium lactate, poly(glyceryl acetate), ectoin and derivatives thereof, chitosan, oligosaccharides and polysaccharides, cyclic carbonates, N-lauroylpyrrolidonecarboxylic acid, and N-α-benzoyl-L-arginine;

or a compound which activates the sebaceous glands, such as steroidal derivatives (including DHEA, 7-oxidized and/or 17-alkylated derivatives thereof and sapogenins), methyl dihydrojasmonate, and vitamin D and derivatives thereof.

According to the invention, glycols, and in particular glycerol, are particularly preferred as moisturizers.

In the case where the compound is a water-soluble polymer, the latter can be chosen from the group made up of an acrylate copolymer, a methacrylate, a polyester and a polyurethane.

The fluid composition may also comprise a visible marker such as a dye or a fluorescent agent, this marker possibly becoming invisible after application to human keratin materials. This can enable the consumer to visualize on the cosmetic composition the exhaustion of the fluid composition, as an indicator for carrying out step b) of the process. The process can comprise the detection of this marker, in particular at the surface of the composition, in order to determine for example the amount of fluid composition remaining on the basic cosmetic composition. The process can then comprise the step consisting in carrying out at least one predefined step depending on the result of this detection. For example, if the marker is no longer detected in a sufficient amount, renewal of step b) can be proposed to the user, or even carried out automatically.

Inkjet Printer

The printer used is of digital type. The term "digital printer" is intended to mean a machine for printing in the form of pixels using digital data, different from a machine comprising a printing form. The printer is an inkjet printer, for example a thermal or piezoelectric printer.

The printer may be a food-grade inkjet printer of the Gatocopy A426 machine type allowing printing onto non-flat objects.

The printing in step a) can be carried out according to a number n of printing passes, with n greater than 1. The higher the printing pass number, the greater the amount of fluid composition deposited. The higher the number of printing passes, the greater the depth of diffusion into the basic composition, i.e. the thicker the impregnated layer. Of course, the diffusion depth also depends on the nature of the basic composition and on that of the fluid composition. Step a) can be carried out in such a way that the impregnated layer is less than 1 mm thick, better still less than 0.5 mm thick.

The number of possible samplings after printing also depends on the number n of printing passes. If the process is carried out in order to test various shades, it is possible to carry out, in step a), a low number of printing passes, for example less than or equal to 10, in particular less than equal to 5, with a given ink colour, thereby allowing just one sampling of composition for testing the shade, before a further printing according to step b) of the process, for example with another ink colour or with a greater amount of ink if the user wishes to retain the shade that he or she has just tried and to have a greater amount of ink with this shade.

When the fluid composition is an ink, the printing can use several different inks, in particular inks of different colours. The printing carried out in step a) of the process may be polychrome printing, in particular trichrome printing or quadrichrome printing, or printing with more than four inks. The printing may use only colouring inks corresponding to primary colours. As a variant, the printing uses both colouring inks corresponding to primary colours and at least one ink corresponding to a non-primary colour. In one variant, the printing may use black and/or white colouring inks Sampling The sampling of the composition after step a) or b) can be carried out with a finger or using a tool such as a cosmetic applicator.

BRIEF DESCRIPTION OF THE DRAWINGS

The invention may be better understood with the following reading of non-limiting implementation examples thereof, and with examination of the attached drawing, in which.

DETAILED DESCRIPTION

Figure 1:
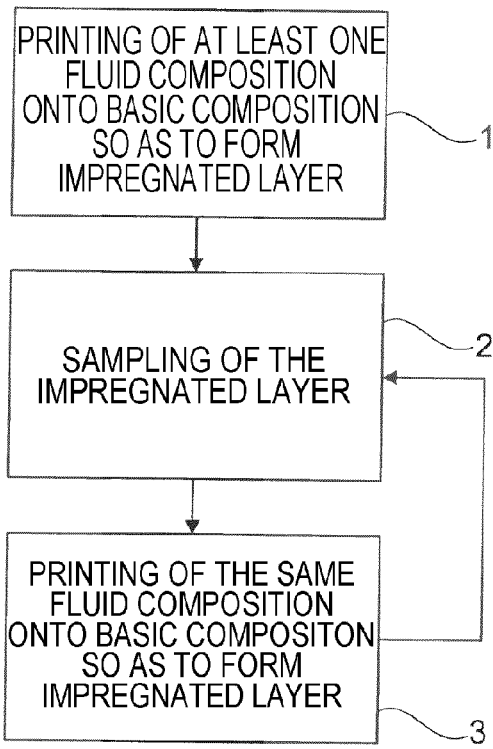
FIG. 1 diagrammatically represents various steps of an example of a process in accordance with the invention, FIG. 2 diagrammatically represents various steps of another example of a process in accordance with the invention.

As illustrated in FIG. 1, an example of a process for producing a cosmetic composition in accordance with the invention comprises a first step 1 consisting in printing at least one fluid composition onto a basic cosmetic composition so as to form an impregnated layer, over only part of the thickness of the basic composition. The fluid composition is for example an ink. Then, in a second step 2, at least one sample is taken, until at least partial wear of the impregnated layer. There may be one or more samplings, depending on the amount sampled by the user at each sampling and depending on the thickness of the impregnated layer.

In a third step 3, the user repeats step 1 with the same fluid composition, in particular the same ink. After sampling of step 2, step 3 can be repeated.

Figure 2:
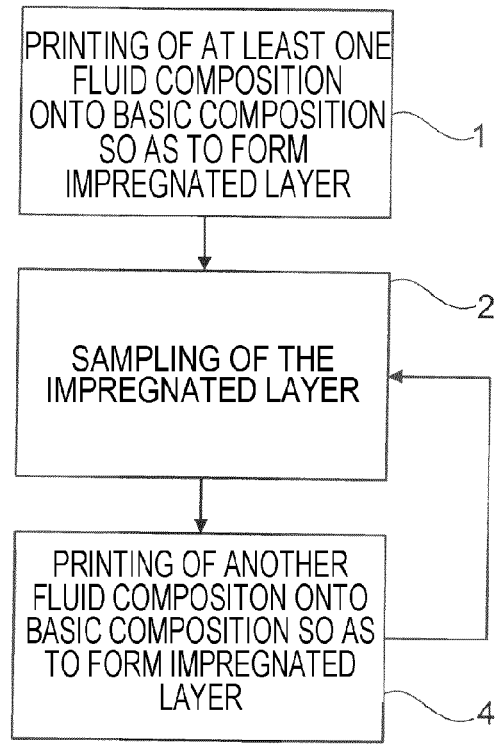

In the example of FIG. 2, in which another example of a process according to the invention is illustrated, the first and second steps 1 and 2 are the same. The final step referenced 4 differs in that a different fluid composition, for example an ink of different colour, is printed onto the basic composition. Steps 4 and 2 can be successively repeated, for example each time with a new colour of ink that is printed.

Figure 3:
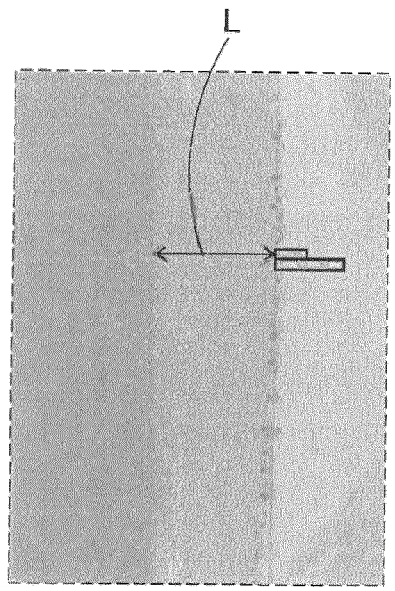
FIG. 3 is a photograph partially showing a cross-section of the basic composition after printing according to the process in accordance with the invention.

Test for Measuring the Thickness of the Layer Impregnated with Fluid Composition After carrying out the printing according to step a) of the process according to the invention, the cosmetic composition impregnated with fluid composition is left to dry for 24 hours. A transverse section is cut in the block of the cosmetic composition using a knife. One of the two halves is freed and a photograph of the slice is taken. It should be noted that it is not possible to measure exactly by means of the slice because of the presence of the small dish. Thus, a photograph, visible in FIG. 3, is taken, with an angle α, in this example equal to 45°, which results in the thickness measured being corrected by a factor $1/\cos(\alpha)$, i.e. 2 if the angle is 45°.

By virtue of a calibration chart and image analysis software, the depth of penetration of the fluid composition, and therefore the thickness L of the layer impregnated with fluid composition, are extracted therefrom.

The work is carried out with a HiROX KH 8700 video microscope equipped with the MX-macro Z VI objective and using proprietary software.

EXAMPLES

Example 1

The following formula is prepared:
Pulverulent Composition 1

| | Compounds | Composition 1 (%) |
|---|---|---|
| FILLERS | TALC (SUPPLIER = IMERYS) | 56.88 |
| | PERLITE (OPTIMA T 2550 OR FROM WORLD MINERAL) | 4.93 |
| | ALUMINIUM STARCH OCTENYLSUCCINATE (SUPPLIER = AKZO NOBEL) | 4.93 |
| | ACRYLONITRILE/METHYL METHACRYLATE/VINYLIDENE CHLORIDE COPOLYMER (EXPANSEL 551 DE40 D42 FROM AKZO NOBEL) | 2.96 |
| | MICA (CI 77019) (SUPPLIER = SCIAMA) | 4.93 |
| | CORN STARCH (CORN STARCH B FROM ROQUETTE) | 7.88 |
| | CLAY (HIGH-VISCOSITY PURIFIED SMECTITE FROM VANDERBILT B) | 2.96 |
| | KAOLINITE (KAOLIN SUPREME FROM IMERYS) | 3.94 |
| | LAUROYL LYSINE (AMIHOPEL FROM AJINOMOTO) | 0.99 |
| FILLER | SILICA MICROBEADS (SILICA BEADS SB 700 FROM MIYOSHI KASEI) | 0.99 |
| | CAPRYLYL GLYCOL | 0.99 |
| | DIMETHICONE (AND) TRIMETHYLSILOXYSILICATE (DOW CORNING 593 FLUID FROM DOW CORNING) | 0.99 |
| | LOW-VISCOSITY DIMETHICONE (XIAMETER PMX-0225 SILICONE FLUID FROM DOW CORNING) | 0.99 |
| BINDERS | GLYCERYL STEARATE (AND) CETYL ALCOHOL (AND) PEG-75 STEARATE (AND) CETETH-20 (AND) STEARETH-20 (EMULIUM DELTA FROM GATTEFOSSE) | 1.97 |
| | SORBITAN ISOSTEARATE (SPAN 120-[LO]-LQ-(MV) FROM | 0.99 |

| Compounds | Composition 1 (%) |
|---|---|
| CRODA) DIMETHICONE (AND) DIMETHICONE/PEG-10/15 CROSSPOLYMER (KSG 210 FROM SHIN-ETSU) | 1.18 |
| WATER | 1.50 |

Each of the compounds is weighed. The compounds are then ground in a Baker mill (paddle: 3000 revolutions/minute; motor 2700 revolutions/minute): the fillers and pigments are mixed for 5 minutes, the nacres are then added and mixed for 5 minutes, and finally the binder is added for 5 minutes. The powder obtained is diluted in water. The amount of water is at 40% by weight relative to the total weight of the composition. The solution obtained is poured into a small dish (reference of the small dish (5×3.5 cm): H250G, amount in small dish: between 8 and 10 g) in 35 mm×50 mm format, lightly pressed using a manual press (pressure: 60 to 80 daN, by placing a screen of pressing net type (screen type: 3 thicknesses of Rimini 150). It is left to dry for at least 8 h, in this example 24 h, at 45° C. while ventilated.

A white-coloured compact is obtained.

The three white-coloured basic compositions, in the form of compact powders contained in small dishes, are introduced into a Gatocopy inkjet printer. Care is taken to position them such that, when the printing is launched, the fluid composition, consisting in this example of ink, comes onto the basic compositions and only onto said compositions.

The inks used are: (manufacturer=Lesepidado):
Ink Epson EU/ME Magenta (ref: ART.76304000)
Ink Epson EU/ME Cyan (ref: ART.76304002)
Ink Epson EU/ME yellow (ref: ART.76304001
Ink Epson EU/ME light Magenta (ref: ART.76304006)
Ink Epson EU/ME light Cyan (ref: ART.76304004)

Printing in 5 passes with three colours, chosen from the first three, is then carried out on each one.

Cosmetic compositions each comprising an impregnated layer of the desired colour and usable without delay are obtained. It is possible to put one's makeup on by sampling the colour with a finger or with a tool.

After five uses, the compositions become white again owing to the wear of the impregnated layer that has been entirely sampled.

Further printing, with new colours, is then carried out.

Example 2

The process is carried out as in Example 1, with the difference that, after the first 5 uses:
the worn zones are detected and recorded,
the printer is programmed so that it prints only on the worn zones, and
the printer is controlled such that it prints, on the worn zones, the same colour as that originally used.

Example 3

The process is carried out in the following way, after Example 1:
the wear caused by each sampling by the user is determined and recorded. To do this, sampling tests are carried out via weighing, before and after, the cosmetic composition so as to deduce there from the amount taken on average by one sampling;
the number of uses that the user wishes to perform is requested;
taking into account the wear that the use causes, the thickness of layer to be impregnated in step a) of the process is deduced therefrom;
the number of printing passes to be carried out is then deduced therefrom.

In another example, a similar test is carried out with the inks chosen from the "light" inks (Ink Epson EU/ME light Magenta (ref: ART.76304006) and Ink Epson EU/ME light Cyan (ref: ART.76304004). Although it is difficult to determine whether wear has been reached (the colour not being very subtle), the amounts sampled are used as a basis to warn the user that a printing must be relaunched.

The invention claimed is:

1. A process for producing a cosmetic composition, comprising the following steps:
   a) inkjet printing onto a basic cosmetic composition, using an inkjet printer, at least one fluid composition in an amount chosen so as to impregnate the basic composition over only a part of its thickness,
   b) removing at least a part of the impregnated layer,
   c) after removing the at least part of the impregnated layer, repeating step a) while optionally modifying the fluid composition inkjet-printed.

2. The process according to claim 1, wherein the amount of the fluid composition printed in step a) is greater than or equal to 5 mg/cm$^2$.

3. The process according to claim 1, wherein the fluid composition is an ink.

4. The process according to claim 3, wherein the printing is polychrome printing.

5. The process according to claim 3, wherein the colour of the fluid composition printed in step a) is different from the colour printed in step c).

6. The process according to claim 1, wherein the fluid composition comprises at least one compound chosen from the group consisting of cosmetic and dermatological active agents, the compound being contained in the fluid composition in a weight concentration of between 0.1% and 40%, relative to the total weight of the fluid composition.

7. The process according to claim 6, wherein the fluid composition further comprises a visible marker that is either a dye or a fluorescent agent, the marker becoming invisible after application to human keratin materials, the process further comprising
detecting the marker present in the cosmetic composition after step b) and
determining the amount of fluid composition remaining on the basic cosmetic composition.

8. The process according to claim 1, the printing being carried out in step a) according to a number n of printing passes that is between 1 and 10.

9. The process according to claim 1, further comprising storing the identity of the printed fluid composition from step a) in an electronic memory.

10. The process according to claim 9, wherein step c) comprises printing the fluid composition whose identity has been stored.

11. The process according to claim 1, the printing being carried out according to information entered by a user or measured on said user's skin.

12. The process according to claim 1, wherein the basic composition is a foundation or a lipstick.

13. The process according to claim 1, further comprising generating information about the depletion of the impregnated layer caused by step b).

14. The process according to claim 1, further comprising identifying the surface portion(s) of the basic composition where the impregnated layer is at least partially exhausted and storing the resulting information in an electronic memory.

15. The process according to claim 14, wherein the printing in step c) only impregnates said surface portion(s).

16. A process for making up human keratin materials comprising
producing a cosmetic composition in accordance with step a) of the process as defined in claim 1,
performing step b) of the process as defined in claim 1 and applying the at least part of the impregnated layer to the keratin materials, and
performing step c) of the process as defined in claim 1.

17. The process according to claim 16, wherein the colour of the fluid composition printed in step a) is different from the colour printed in step c).

18. The process according to claim 16, wherein the colour of the fluid composition printed in step a) is the same as the colour printed in step c), further comprising printing the fluid composition of step c) in an amount greater than the amount initially printed in step a).

19. The process according to claim 6, wherein the at least one compound is chosen from the group consisting of fragrances, UV-screening agents, moisturizers, binders, and mixtures thereof.

* * * * *